(12) United States Patent
De Kock et al.

(10) Patent No.: US 11,471,190 B2
(45) Date of Patent: Oct. 18, 2022

(54) BUNDLE OF HIS LEAD DELIVERY CATHETER, SYSTEM AND METHOD

(71) Applicant: Cardiac Pacemakers, Inc., St. Paul, MN (US)

(72) Inventors: Andrew L. De Kock, Ham Lake, MN (US); G. Shantanu Reddy, Minneapolis, MN (US); Newell G. Voss, Woodbury, MN (US); Lili Liu, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 404 days.

(21) Appl. No.: 16/373,199

(22) Filed: Apr. 2, 2019

(65) Prior Publication Data

US 2019/0298990 A1   Oct. 3, 2019

Related U.S. Application Data

(60) Provisional application No. 62/651,571, filed on Apr. 2, 2018.

(51) Int. Cl.
*A61B 17/34* (2006.01)
*A61N 1/05* (2006.01)
(Continued)

(52) U.S. Cl.
CPC ..... *A61B 17/3468* (2013.01); *A61M 25/0041* (2013.01); *A61N 1/05* (2013.01);
(Continued)

(58) Field of Classification Search
CPC ...... A61B 17/3468; A61B 2017/00292; A61N 1/05
See application file for complete search history.

(56) References Cited

U.S. PATENT DOCUMENTS 4,508,535 A * 4/1985 Joh .................. A61M 1/3659
604/532
4,882,777 A 11/1989 Narula
(Continued)

FOREIGN PATENT DOCUMENTS

CN     101528145 A    9/2009
CN     102281819 A    12/2011
(Continued)

OTHER PUBLICATIONS

Calvi, Valeria et al., "Incidence rate and predictors of permanent pacemaker implantation after transcatheter aortic valve implantation with self-expanding CoreValve prosthesis", Journal Interv Card Electrophysiol, Nov. 26, 2011, 7 pages.
(Continued)

*Primary Examiner* — Alexander J Orkin
(74) *Attorney, Agent, or Firm* — Nelson Mullins Riley & Scarborough LLP

(57) ABSTRACT

A catheter for delivering a medical electrical lead to a bundle of His from within a right atrium of a heart. The catheter includes a straight portion and a hook portion projecting from a distal end of the straight portion. The hook portion includes a first curved portion, a second curved portion, and a third curved portion. The straight portion and the first curved portion define a plane. The second curved portion extends from a distal end of the first curved portion. The second curved portion curves away from the plane. The third curved portion extends from a distal end of the second curved portion. The third curved portion curves toward the plane. The catheter forms a lumen extending from a proximal end of the straight portion to an opening at a distal end of the third curved portion.

15 Claims, 9 Drawing Sheets

(51) Int. Cl.
  *A61N 1/362* (2006.01)
  *A61M 25/00* (2006.01)
  *A61N 1/372* (2006.01)
  *A61B 17/00* (2006.01)

(52) U.S. Cl.
  CPC ............. *A61N 1/056* (2013.01); *A61N 1/362* (2013.01); *A61N 1/372* (2013.01); *A61B 2017/00292* (2013.01); *A61M 25/0068* (2013.01)

(56) References Cited

U.S. PATENT DOCUMENTS

| | | | |
|---|---|---|---|
| 5,401,258 A * | 3/1995 | Voda | A61M 25/0041 604/523 |
| 5,427,119 A | 6/1995 | Swartz et al. | |
| 5,497,774 A | 3/1996 | Swartz et al. | |
| 5,564,440 A | 10/1996 | Swartz et al. | |
| 5,628,316 A | 5/1997 | Swartz et al. | |
| 5,640,955 A | 6/1997 | Ockuly et al. | |
| 5,715,818 A | 2/1998 | Swartz et al. | |
| 5,722,400 A | 3/1998 | Ockuly et al. | |
| 5,810,730 A | 9/1998 | Swartz et al. | |
| 5,814,028 A | 9/1998 | Swartz et al. | |
| 5,833,673 A | 11/1998 | Ockuly et al. | |
| 5,868,733 A | 2/1999 | Ockuly et al. | |
| 5,879,296 A | 3/1999 | Ockuly et al. | |
| 5,902,289 A | 5/1999 | Swartz et al. | |
| 6,066,125 A * | 5/2000 | Webster, Jr. | A61B 5/015 604/528 |
| 6,090,084 A | 7/2000 | Hassett et al. | |
| 6,122,552 A | 9/2000 | Tockman et al. | |
| 6,156,018 A | 12/2000 | Hassett | |
| 6,203,531 B1 | 3/2001 | Ockuly et al. | |
| 6,224,557 B1 | 5/2001 | Ziel et al. | |
| 6,296,630 B1 | 10/2001 | Altman et al. | |
| 6,937,897 B2 | 8/2005 | Min et al. | |
| 7,547,301 B2 | 6/2009 | Altman et al. | |
| 7,647,124 B2 | 1/2010 | Williams | |
| 7,729,782 B2 | 6/2010 | Williams et al. | |
| 7,815,577 B2 | 10/2010 | Krishnan | |
| 8,326,423 B2 | 12/2012 | Zhu et al. | |
| 8,346,358 B2 | 1/2013 | Ortega et al. | |
| 8,406,899 B2 | 3/2013 | Reddy et al. | |
| 8,423,139 B2 | 4/2013 | Zhu et al. | |
| 8,437,848 B2 | 5/2013 | Ortega et al. | |
| 8,509,916 B2 | 8/2013 | Byrd et al. | |
| 8,606,369 B2 | 12/2013 | Williams et al. | |
| 8,812,106 B2 | 8/2014 | Ortega et al. | |
| 8,825,159 B2 | 9/2014 | Zhu et al. | |
| 8,834,384 B2 | 9/2014 | Krishnan | |
| 8,874,237 B2 | 10/2014 | Schilling | |
| 8,939,960 B2 | 1/2015 | Rosenman et al. | |
| 9,008,768 B2 | 4/2015 | Zhu et al. | |
| 2004/0006268 A1 | 1/2004 | Gilboa et al. | |
| 2004/0064176 A1 | 4/2004 | Min et al. | |
| 2004/0116878 A1 | 6/2004 | Byrd et al. | |
| 2005/0096589 A1 | 5/2005 | Shachar | |
| 2005/0124881 A1 | 6/2005 | Kanai et al. | |
| 2006/0009827 A1 | 1/2006 | Kurth et al. | |
| 2006/0095030 A1 * | 5/2006 | Avitall | A61B 18/1492 606/41 |
| 2006/0106445 A1 | 5/2006 | Woollett | |
| 2006/0142812 A1 | 6/2006 | Ortega et al. | |
| 2006/0276710 A1 | 12/2006 | Krishnan | |
| 2007/0112405 A1 | 5/2007 | Williams et al. | |
| 2007/0165916 A1 | 7/2007 | Cloutier et al. | |
| 2007/0203555 A1 | 8/2007 | Williaims | |
| 2008/0015542 A1 | 1/2008 | Altman et al. | |
| 2008/0082136 A1 | 4/2008 | Gaudiani | |
| 2008/0221566 A1 | 9/2008 | Krishnan | |
| 2008/0287803 A1 | 11/2008 | Li et al. | |
| 2008/0287918 A1 | 11/2008 | Rosenman et al. | |
| 2008/0319499 A1 | 12/2008 | Zhu et al. | |
| 2009/0005846 A1 | 1/2009 | Zhu et al. | |
| 2009/0093859 A1 | 4/2009 | Ortega et al. | |
| 2009/0248045 A1 | 10/2009 | Trovato | |
| 2009/0259272 A1 | 10/2009 | Reddy et al. | |
| 2009/0264780 A1 | 10/2009 | Schilling | |
| 2010/0305579 A1 | 12/2010 | Williams et al. | |
| 2011/0077507 A1 | 3/2011 | Krishnan | |
| 2012/0179221 A1 | 7/2012 | Reddy et al. | |
| 2012/0232563 A1 | 9/2012 | Williams et al. | |
| 2013/0184774 A1 | 7/2013 | Zhu et al. | |
| 2013/0261689 A1 | 10/2013 | Zhu et al. | |
| 2013/0261690 A1 | 10/2013 | Ortega et al. | |
| 2014/0067036 A1 | 3/2014 | Shuros et al. | |
| 2014/0088566 A1 * | 3/2014 | Dangoisse | A61M 25/0041 604/532 |
| 2017/0266415 A1 * | 9/2017 | Lampropoulos | A61B 17/3468 |
| 2018/0078772 A1 * | 3/2018 | Williams | A61N 1/372 |

FOREIGN PATENT DOCUMENTS

| | | |
|---|---|---|
| EP | 2274046 A2 | 1/2011 |
| EP | 2275170 A1 | 1/2011 |
| EP | 2526997 A1 | 11/2012 |
| EP | 2890444 A2 | 7/2015 |
| JP | 2006-506211 A | 2/2006 |
| JP | 2010-503449 A | 2/2010 |
| WO | 2004/028621 A2 | 4/2004 |
| WO | 2009/129313 A2 | 10/2009 |
| WO | 2009/135075 A1 | 11/2009 |
| WO | 2012/121817 A1 | 9/2012 |
| WO | 2014/036317 A2 | 3/2014 |
| WO | 2018/052597 A1 | 3/2018 |

OTHER PUBLICATIONS

Dandamudi, G. and Vijayaraman, P. (2016). How to perform permanent His bundle pacing in routine clinical practice. Heart Rhythm Society, 13:1362-1366.

Fraccaro, Chiara et al., "Incidence, Predictors, and outcome of Conduction Disorders After Transcatheter Self-Expandable Aortic Valve Implantation", The American Journal of Cardiology, Mar. 1, 2011, vol. 107, pp. 747-754.

International Search Report and Written Opinion issued in PCT/US2013/057381, dated Apr. 15, 2014, 17 pages.

International Search Report and Written Opinion received for PCT Patent Application No. PCT/US2019/025375, dated Jul. 12, 2019, 8 pages.

\* cited by examiner

BUNDLE OF HIS LEAD DELIVERY CATHETER, SYSTEM AND METHOD

CROSS REFERENCE TO RELATED APPLICATIONS

This application claims the benefit of U.S. Provisional Patent Application Ser. No. 62/651,571, filed Apr. 2, 2018, entitled BUNDLE OF HIS LEAD DELIVERY CATHETER, SYSTEM AND METHOD, the disclosure of which is incorporated by reference herein in its entirety.

TECHNICAL FIELD

The present disclosure relates to medical electrical lead delivery catheters, systems, and methods. In particular, the present disclosure relates to catheters, systems, and methods for delivering a medical electrical lead to the bundle of His from the right atrium.

BACKGROUND

Cardiac rhythm management systems are useful for electrically stimulating a patient's heart to treat various cardia arrhythmias. Stimulating the bundle of His may prevent dyssynchrony which may be associated with right ventricular apex pacing which can result in asynchronous delayed activation of the heart and compromised hemodynamics. Normal His-Purkinje activation of the myocardium can lead to rapid sequential synchronous multi-site depolarization of myocardial cells and efficient ventricular contraction in patients with intact His-Purkinje function. There is a continuing need for improved medical electrical lead delivery catheters, systems, and methods for targeting the bundle of His.

SUMMARY

Example 1 is a catheter for delivering a medical electrical lead to a bundle of His from within a right atrium of a heart. The catheter includes a straight portion and a hook portion projecting from a distal end of the straight portion. The hook portion includes a first curved portion, a second curved portion, and a third curved portion. The straight portion and the first curved portion define a plane. The second curved portion extends from a distal end of the first curved portion. The second curved portion curves away from the plane. The third curved portion extends from a distal end of the second curved portion. The third curved portion curves toward the plane. The catheter forms a lumen extending from a proximal end of the straight portion to an opening at a distal end of the third curved portion.

Example 2 is the catheter of Example 1, wherein the first curved portion and the second curved portion define a compound curve when projected onto the plane, and the third curved portion has a reversal of curvature from the compound curve when projected onto the plane.

Example 3 the catheter of either of Examples 1 or 2, wherein the catheter is configured to be introduced transvascularly into the heart, extend down a lateral wall of a superior vena cava, and across the right atrium so that the opening at a distal end of the hook portion is disposed perpendicularly to a portion of an atrioventricular septum adjacent to the bundle of His.

Example 4 is the catheter of Example 3, wherein the first curved portion includes a bottom of the hook portion.

Example 5 is the catheter of either of Examples 3 or 4, wherein the first curved portion extends from the distal end of the straight portion.

Example 6 is the catheter of any of Examples 3-5, wherein a length of the first curved portion is greater than a length of the second curved portion.

Example 7 is the catheter of either of Examples 1 or 2, wherein the catheter is configured to be introduced transvascularly into the heart, extend down a right lateral wall of the right atrium toward a floor of the right atrium, and extend anterio-medial away from the floor of the right atrium so that the opening at a distal end of the third curved portion is disposed perpendicularly to a portion of an atrioventricular septum adjacent to the bundle of His.

Example 8 is the catheter of Example 7, wherein the second curved portion includes a bottom of the hook portion.

Example 9 is the catheter of either of Examples 7 or 8, further including a fourth curved portion extending from the distal end of the straight portion, the first curved portion extending from a distal end of the fourth curved portion, the fourth curved portion coplanar with the first curved portion and having a reversal of curvature from the first curved portion when projected onto the plane.

Example 10 is the catheter of any of Examples 7-9, wherein a length of the second curved portion is greater than a length of the first curved portion.

Example 11 is the catheter of Example 1, wherein the first curved portion, the second curved portion and the third curved portion define a compound curve when projected onto the plane, the third curved portion extending toward the first curved portion and across the plane.

Example 12 is the catheter of any of Examples 1-11, wherein the first curved portion and the second curved portion have a radius of curvature greater than 17 millimeters.

Example 13 is the catheter of any of Examples 1-12, wherein the hook portion has a radius of curvature greater than 17 millimeters.

Example 14 is a system for delivering a medical electrical lead to a bundle of His from within a right atrium of a heart. The system includes a catheter according to any of Examples 1-13 and the medical electrical lead configured to pass through the lumen.

Example 15 is the system of Example 14, wherein the medical electrical lead includes an active fixation element.

Example 16 is a catheter for delivering a medical electrical lead to a bundle of His from within a right atrium of a heart. The catheter includes a straight portion and a hook portion projecting from a distal end of the straight portion. The hook portion includes a first curved portion, a second curved portion, and a third curved portion. The straight portion and the first curved portion define a plane. The second curved portion extends from a distal end of the first curved portion. The second curved portion curves away from the plane. The second curved portion has a radius of curvature greater than 17 millimeters. The third curved portion extends from a distal end of the second curved portion. The third curved portion curves toward the plane. The catheter forms a lumen extending from a proximal end of the straight portion to an opening at a distal end of the third curved portion.

Example 17 the catheter of Example 16, wherein the first curved portion and the second curved portion define a compound curve when projected onto the plane, and the third curved portion has a reversal of curvature from the compound curve when projected onto the plane.

Example 18 the catheter of either of Examples 16 or 17, wherein the catheter is configured to be introduced transvascularly into the heart, extend down a lateral wall of a superior vena cava, and across the right atrium so that the opening at a distal end of the hook portion is disposed perpendicularly to a portion of an atrioventricular septum adjacent to the bundle of His.

Example 19 the catheter of Example 18, wherein the first curved portion includes a bottom of the hook portion.

Example 20 the catheter of either of Examples 18 or 19, wherein the first curved portion extends from the distal end of the straight portion.

Example 21 the catheter of any of Examples 18-20, wherein a length of the first curved portion is greater than a length of the second curved portion.

Example 22 the catheter of either of Examples 16 or 17, wherein the catheter is configured to be introduced transvascularly into the heart, extend down a right lateral wall of the right atrium toward a floor of the right atrium, and extend anterio-medial away from the floor of the right atrium so that the opening at the distal end of the hook portion is disposed perpendicularly to a portion of an atrioventricular septum adjacent to the bundle of His.

Example 23 the catheter of Example 22, wherein the second curved portion includes a bottom of the hook portion.

Example 24 the catheter of either of Examples 22 or 23, further including a fourth curved portion extending from the distal end of the straight portion, the first curved portion extending from a distal end of the fourth curved portion, the fourth curved portion coplanar with the first curved portion and having a reversal of curvature from the first curved portion when projected onto the plane.

Example 25 the catheter of any of Examples 22-24, wherein a length of the second curved portion is greater than a length of the first curved portion.

Example 26 the catheter of Example 16, wherein the first curved portion, the second curved portion and the third curved portion define a compound curve when projected onto the plane, the third curved portion extending toward the first curved portion and across the plane.

Example 27 the catheter of any of Examples 16-26, wherein the hook portion has a radius of curvature greater than 17 millimeters.

Example 28 is a system for delivering a medical electrical lead to a bundle of His from within a right atrium of a heart. The system includes a catheter and the medical electrical lead. The catheter includes a straight portion and a hook portion projecting from a distal end of the straight portion. The hook portion includes a first curved portion, a second curved portion, and a third curved portion. The straight portion and the first curved portion define a plane. The second curved portion extends from a distal end of the first curved portion. The second curved portion curves away from the plane. The second curved portion has a radius of curvature greater than 17 millimeters. The third curved portion extends from a distal end of the second curved portion. The third curved portion curves toward the plane. The catheter forms a lumen extending from a proximal end of the straight portion to an opening at a distal end of the third curved portion. The medical electrical lead is configured to pass through the lumen.

Example 29 the system of Example 28, wherein the medical electrical lead includes an active fixation element.

Example 30 the system of either of Examples 28 or 28, wherein the first curved portion and the second curved portion define a compound curve when projected onto the plane, and the third curved portion has a reversal of curvature from the compound curve when projected onto the plane.

Example 31 the system of any of Examples 28-30, further including a fourth curved portion extending from the distal end of the straight portion, the first curved portion extending from a distal end of the fourth curved portion, the fourth curved portion coplanar with the first curved portion and having a reversal of curvature from the first curved portion when projected onto the plane.

Example 32 the system of Example 28, wherein the first curved portion, the second curved portion and the third curved portion define a compound curve when projected onto the plane, the third curved portion extending toward the first curved portion and across the plane.

Example 33 is a method of implanting a medical electrical lead to stimulate a bundle of His. The method includes introducing a catheter transvascularly through a superior vena cava and into a right atrium of a heart, a hook portion of the catheter configured such that an opening at a distal end of the hook portion oriented to face a surface of an atrioventricular septum adjacent to the bundle of His; extending a fixation element on a distal tip of the medical electrical lead from the opening at the distal end of the hook portion; locating tissue of a target site along the atrioventricular septum; deploying the fixation element in the tissue of the target site to implant the medical electrical lead in contact with the bundle of His; and removing the catheter from over the medical electrical lead.

Example 34 the method of Example 33, wherein introducing the catheter transvascularly into the heart includes disposing the hook portion within the heart such that it extends down a lateral wall of a superior vena cava, and across the right atrium so that the opening at the distal end of the hook portion is disposed perpendicularly to a portion of the atrioventricular septum adjacent to the bundle of His.

Example 35 the method of Example 33, wherein introducing the catheter transvascularly into the heart includes disposing the hook portion within the heart such that it extends down a right lateral wall of the right atrium toward a floor of the right atrium, and extends anterio-medial away from the floor of the right atrium so that the opening at the distal end of the hook portion is disposed perpendicularly to the portion of the atrioventricular septum adjacent to the bundle of His.

While multiple examples are disclosed, still other examples in accordance with this disclosure will become apparent to those skilled in the art from the following detailed description, which shows and describes illustrative embodiments. Accordingly, the drawings and detailed description are to be regarded as illustrative in nature and not restrictive.

Figure 1:
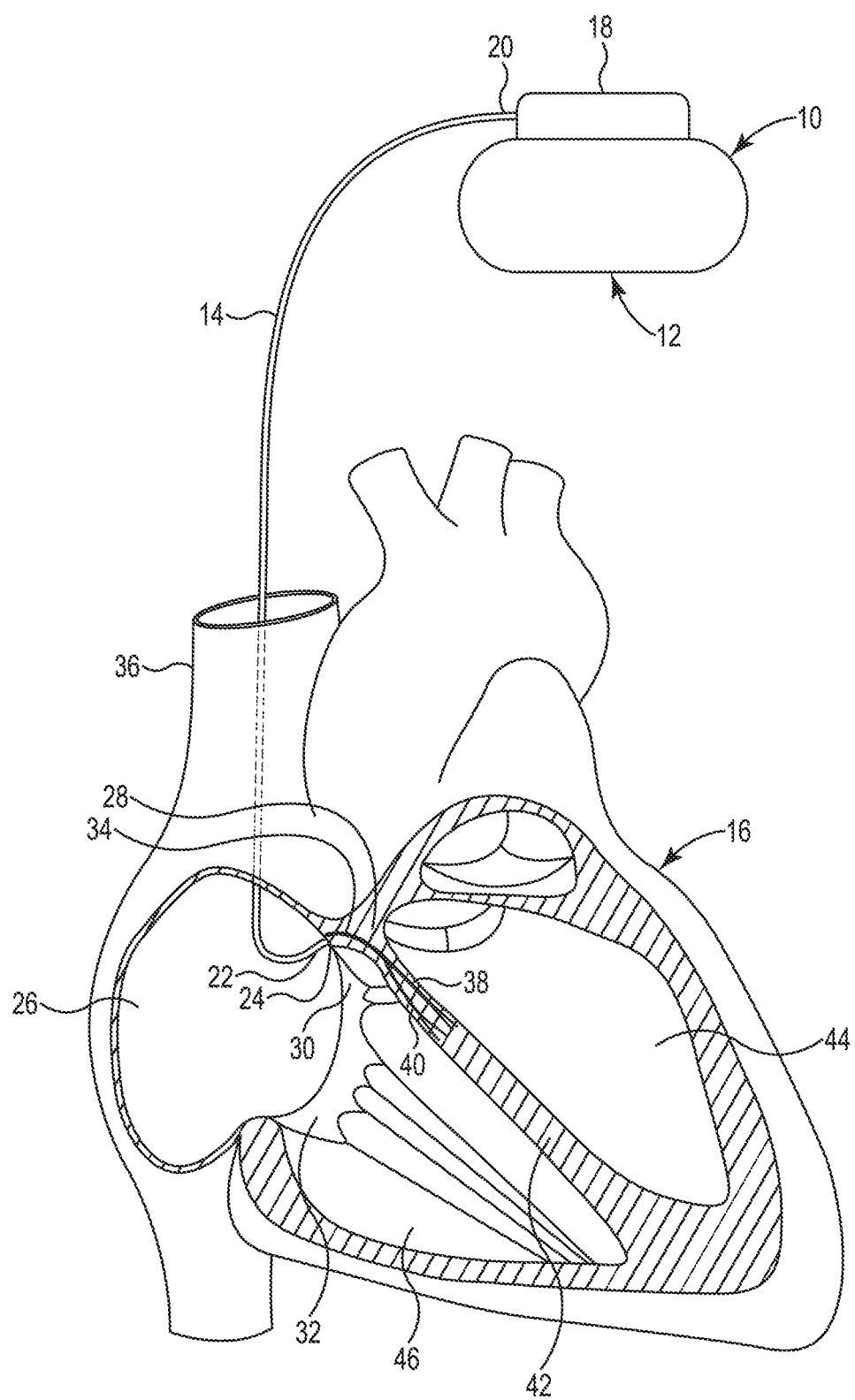
FIG. 1 is a schematic diagram of a His bundle stimulation system, according to some embodiments of this disclosure.

While this disclosure is amenable to various modifications and alternative forms, specific embodiments have been shown by way of example in the drawings and are described in detail below. The intention, however, is not to limit the disclosure to the particular embodiments described. On the contrary, this disclosure is intended to cover all modifications, equivalents, and alternatives falling within the scope of the disclosure as defined by the appended claims.

DETAILED DESCRIPTION

The output of the heart is dependent on the synchrony of contraction within, and between, the chambers of the heart. Normally, each cardiac cycle is initiated by the depolarization of cells in the sinoatrial node which starts contraction of the cardiac muscle cells of the atria. The electrical impulse continues to the atrioventricular node, which delays propagation of the signal to allow the atria to contract before the ventricles. The distal portion of the atrioventricular node comprises the bundle of His. The bundle of His propagates the depolarization signal to left and right branches in the interventricular septum. The left and right branches propagate the depolarization signal to the Purkinje fibers of the left and right ventricles, respectively.

Various conditions can interfere with the normal electrical conduction system of the heart, which can result in arrhythmia and can compromise the output of the heart. For example, conduction block along the atrioventricular node can cause the atria and ventricles to contract out of rhythm. Conventional pacing therapies attempt to bypass the conduction system between the atria and ventricles by implanting a lead in the apex of the right ventricle where, ideally, each pulse delivered to cardiac muscle tissue propagates in a depolarization wave. However, direct stimulation of working myocardium (e.g., at the apex of the right ventricle) can result in slower propagation than direct stimulation of the specialized conduction system fibers, the His-Purkinje system. For these and other reasons, it can be difficult to replicate the synchronous contractions of a natural conduction system by pacing at the apex of the right ventricle or other working myocardial site alone.

The present disclosure concerns, among other things, using the heart's specialized conduction system by targeting the bundle of His for direct stimulation. In particular, the present disclosure concerns securing one or more electrodes in contact with, or proximate, the nerve fibers of the bundle of His. The bundle of His can be accessed from multiple areas. One area is along the atrioventricular septum in the right atrium at the apex of the Triangle of Koch. The Triangle of Koch is a roughly triangular are on the septal wall of the right atrium, bounded by the base of the septal leaflet of the tricuspid valve, the anteromedial margin of the orifice of the coronary sinus, and the tendon of Todaro. His capture can be obtained by a pacing lead fixated properly at the apex of the Triangle of Koch.

Delivery catheters according to embodiments of this disclosure are shaped to facilitate placement of a medical electrical lead in the right atrium, at the atrioventricular septum, just above, and superior to, the septal leaflet of the tricuspid valve.

FIG. 1 is a schematic diagram of a His bundle stimulation system, according to some embodiments of this disclosure. FIG. 1 illustrates a stimulation system 10 including an implantable pulse generator 12 and a lead 14. The lead 14 is implanted in a heart 16. The implantable pulse generator 12 can include circuitry for sensing bioelectrical signals and/or delivering electrical stimulation via the lead 14. The implantable pulse generator 12 can include a lead interface 18 (e.g., a header). The lead 14 can include a proximal end 20, a distal end 22, and a fixation element 24 disposed at the distal end 22.

The lead 14 can further include one or more electrical contacts (not shown) at the proximal end 20, one or more electrical elements (e.g. ring electrodes) at the distal end 22, and one or more electrical conductors (e.g., one or more coils or one or more cable conductors) (not shown) extending within a lumen 73 (FIG. 3) extending within the lead 14 from the electrical contacts to the electrical elements. The lead interface 18 can connect the pulse generator 12 to the electrical contacts at the proximal end 20 of the lead 14 to electrically connect the pulse generator 12 to the electrical elements.

As shown in FIG. 1, the lead 14 is implanted in a right atrium 26, at an atrioventricular septum 28, just above a septal leaflet 30 of a tricuspid valve 32 for directly stimulating a bundle of His 34. The lead 14 operates to convey electrical signals between the bundle of His 34 and the implantable pulse generator 12. In some embodiments, the lead 14 can enter the vascular system through a vascular entry site (not shown) formed in a wall of the left subclavian vein (not shown), extend through the left brachiocephalic vein (not shown) and the superior vena cava 36, to the right atrium 26. Other suitable vascular access sites may be used in various other embodiments.

The fixation element 24 can fix the lead 14 to cardiac tissue, such as the area of tissue by which the bundle of His 34 can be directly stimulated. In some embodiments, the fixation element 24 can be electrically coupled to the implantable pulse generator 12 by, for example, one of the electrical conductors, such as a coil, extending to the proximal end 20 of the lead 14 for interfacing with the lead interface 18. As such, the fixation element 24 can mechanically and electrically couple the lead 14 to the tissue and facilitate the transmission of electrical energy from the bundle of His 34 in a sensing mode and to the bundle of His 34 in a stimulation mode. In some embodiments, the fixation element 24 is a fixed fixation element, such as helix fixed to the lead 14. Such a fixation element 24 can be deployed by rotating the lead 14 itself to implant the fixation element 24 into the tissue. In some other embodiments, the fixation element 24 can be an active fixation element, such as a helix or one more tines. Such an active fixation element can be deployed by rotating the connected coil at the proximal end 20 which transmits torque along the coil to rotate the fixation element 24 and implant the fixation element 24 into the tissue without having to rotate the lead 14 itself. The use of the active fixation element for the fixation element 24 may allow for more precise placement of the lead 14. The use of the active fixation element for the fixation element 24 may also provide for better mapping capability because the user need not be concerned with accidental entanglement of the helix in the tissue.

While the placement of the lead 14 at various locations may be able to indirectly stimulate the bundle of His 34, placing the lead 14 with one or more electrodes, such as the fixation element 24, in contact with the fibers of the bundle of His 34, or immediately proximate to the fibers of the bundle of His 34 (e.g., within 5 millimeters), can reliably capture the tissue of the bundle of His 34 (i.e., cause the cells to depolarize and propagate an activation signal) with a pace pulse. For example, the fixation element 24 in contact with the bundle of His 34 can capture the bundle of His 34 above a left ventricular branch 38 and a right ventricular branch 40 of the specialized conduction system, thereby causing a depolarization wave to travel down a septum 42 along both left 38 and right 40 branches. The depolarization wave can spread to the working myocardial tissue of a left ventricle 44 and a right ventricle 46, causing the left ventricle 44 and the right ventricle 46 to contract.

While FIG. 1 only shows a single lead connected to the implantable pulse generator 12 and implanted for cardiac stimulation, various other embodiments can have an alternative lead and/or one or more additional leads for sensing bioelectrical activity and/or stimulating the bundle of His 34 or other areas of the heart 16.

As discussed herein, delivering a lead to a target in the right atrium 26, at the atrioventricular septum 28, just above the septal leaflet 30 of the tricuspid valve 32 can be a difficult procedure. The small area of tissue that provides access to the bundle of His 34 must first be located. The target can be located by a catheter with an electrode sensing an electrical biomarker indicative of the electrical activation of the bundle of His in a mapping procedure. The biomarker is typically weak and only emerges if the signal is sensed by an electrode proximate the bundle of His (e.g., by sensing the biomarker as a near field signal). In various cases, the one or more electrodes of the mapping catheter will need to be in contact with the tissue that provides access to the bundle of His. Once located by the mapping catheter, a lead must be advanced to the small area. The location of the small area can be lost while the mapping catheter is exchanged for the lead and/or before the lead can be affixed to the small area. However, the catheters, systems, and methods disclosed herein can facilitate the accurate placement and stabilization of the lead 14 at the target location.

Figure 2:
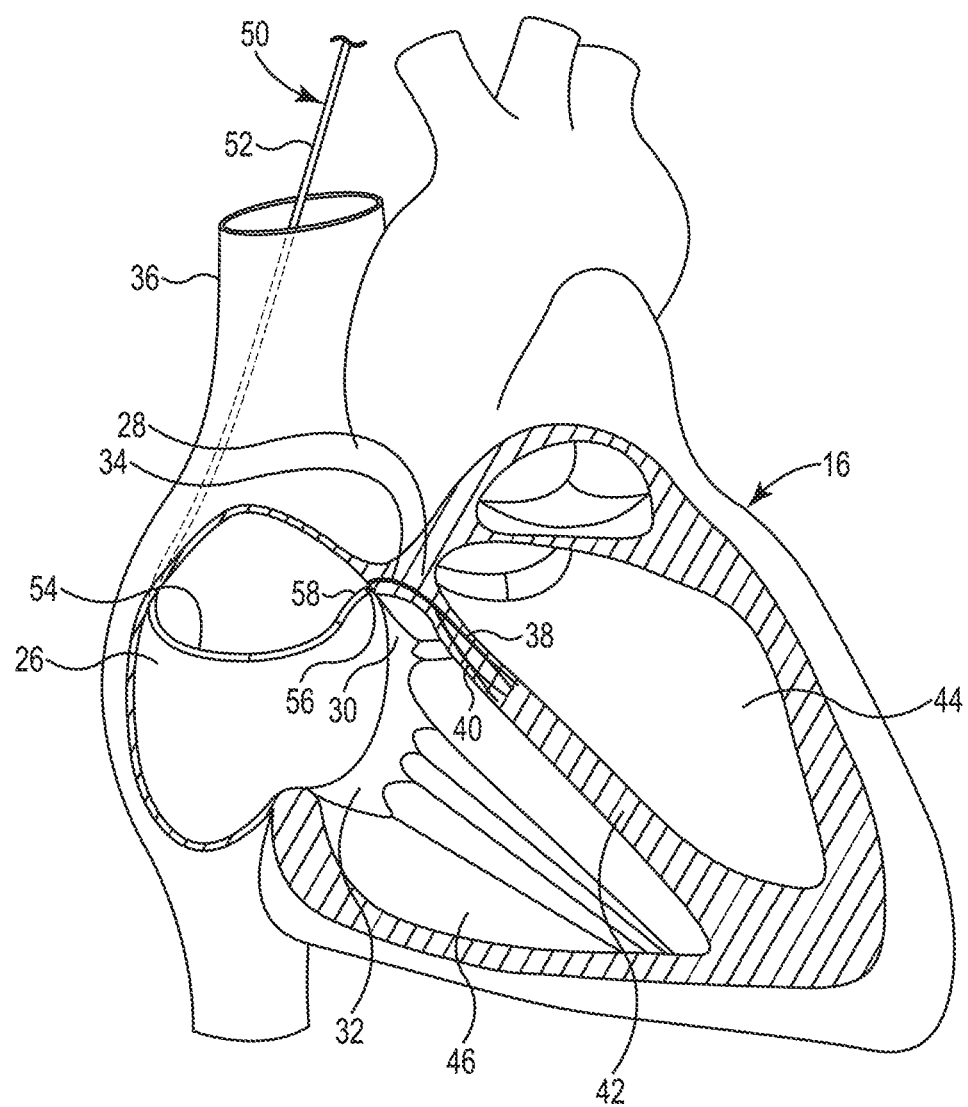
FIG. 2 is a schematic diagram of a catheter for delivering a medical electrical lead to a bundle of His from within the right atrium, according to some embodiments of this disclosure.

FIG. 2 is a schematic diagram of a catheter for delivering a medical electrical lead to a bundle of His from within the right atrium, according to some embodiments of this disclosure. FIG. 2 shows a catheter 50 including a straight portion 52 and a hook portion 54. The hook portion 54 can project from the straight portion 52. The catheter 50 can be introduced transvascularly into the heart 16 as described above for the lead 14 in reference to FIG. 1. The catheter 50 is configured, as described below in reference to FIGS. 3-5, to extend down a lateral wall of the superior vena cava 36 and across the right atrium 26 so that an opening 56 at a distal end 58 of the hook portion 54 is disposed perpendicularly to a portion of the atrioventricular septum 28 adjacent to the bundle of His 34. So oriented, the lead 14 passing through the catheter 50 can be accurately delivered to the target site for implantation.

Figure 3:
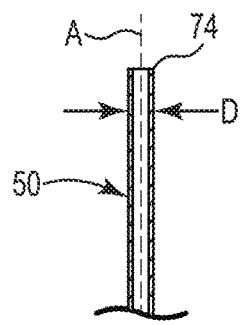
FIG. 3 is a side view of the catheter of FIG. 2 for delivering a medical electrical lead to a bundle of His from within a right atrium, according to some embodiments of this disclosure.
Figure 3:
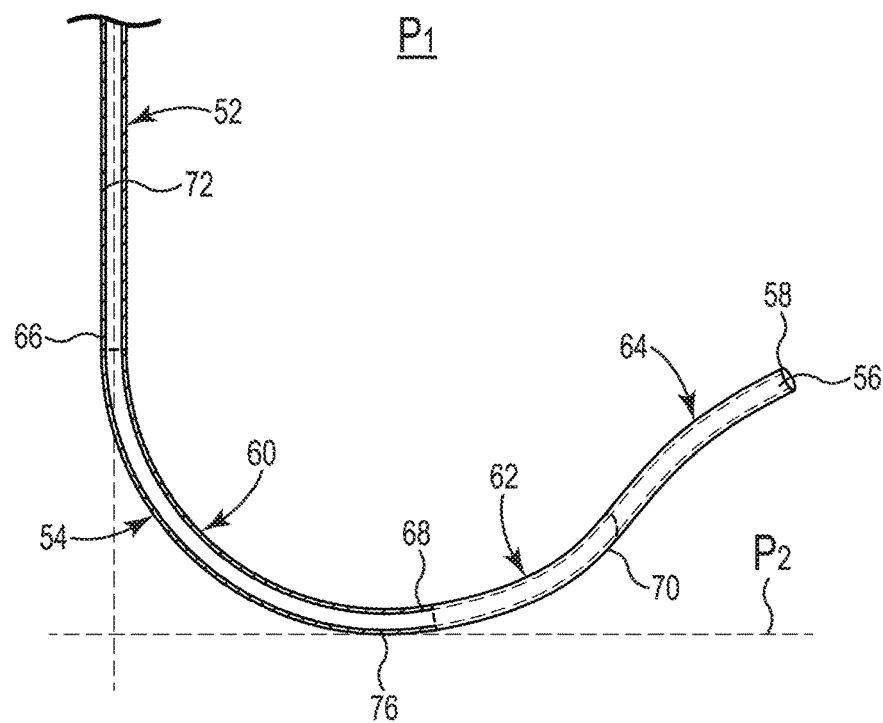
Figure 4:
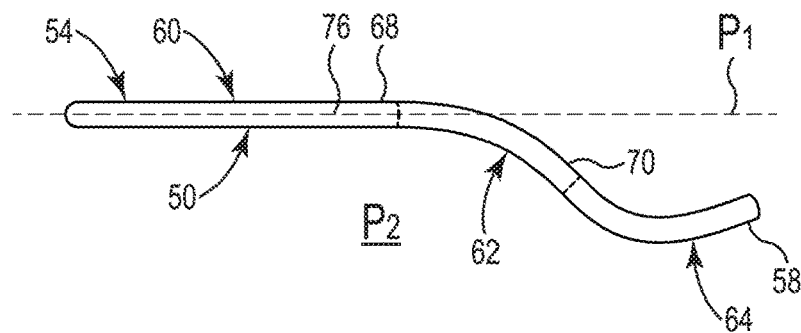
FIG. 4 is a bottom view of the catheter shown in FIG. 3, according to some embodiments of this disclosure.
Figure 5:
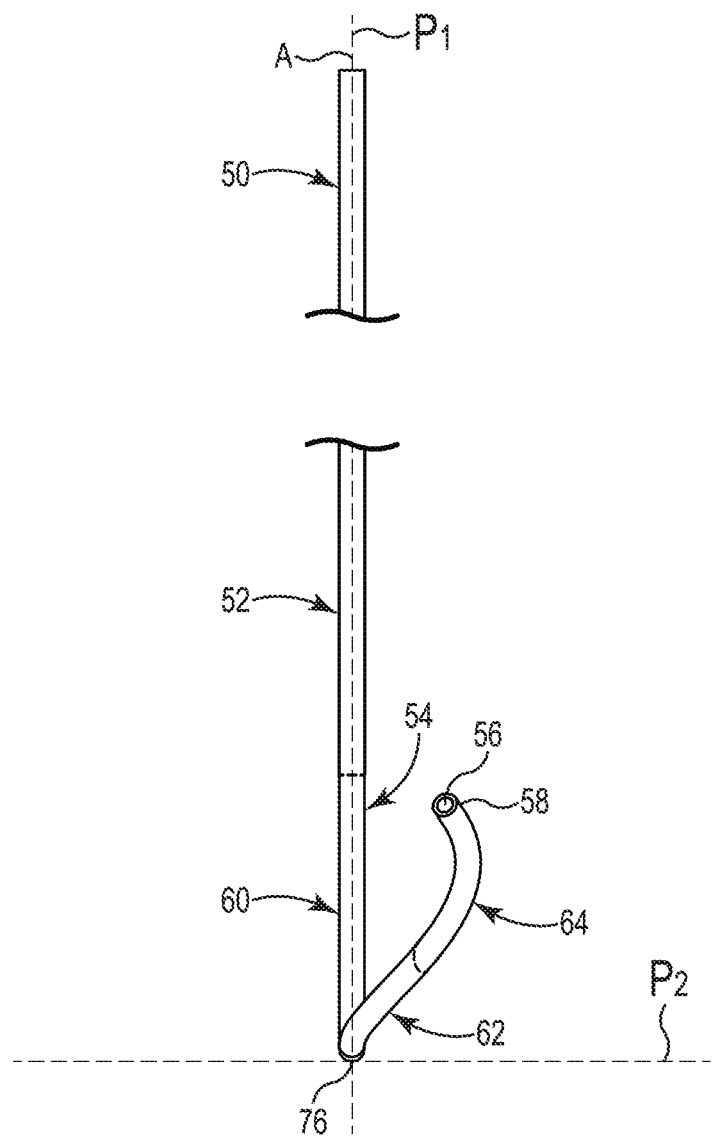
FIG. 5 is another side view of the catheter shown in FIGS. 3 and 4, according to some embodiments of this disclosure.

FIG. 3 is a side view of the catheter 50 of FIG. 2 for delivering a medical electrical lead to a bundle of His from within a right atrium, according to some embodiments of this disclosure. FIG. 3 shows the catheter 50 including the straight portion 52 and the hook portion 54. The hook portion 54 can include a first curved portion 60, a second curved portion 62, and a third curved portion 64. The hook portion 54 can project from a distal end 66 of the straight portion 52. The first curved portion 60 can extend from the distal end 66 of the straight portion 52. The second curved portion 62 can extend from a distal end 68 of the first curved portion 60. The third curved portion 64 can extend from a distal end 70 of the second curved portion 62. In some embodiments, the third curved portion 64 can include the opening 56 at the distal end 58 of the hook portion 54, as shown in FIG. 3. The straight portion 52 and the first curved portion 60 can define a plane $P_1$. The second curved portion 62 can curve away from the plane $P_1$, as shown in FIGS. 4 and 5, described below. The third curved portion 64 can curve back toward the plane $P_1$, as also shown in FIGS. 4 and 5. In FIG. 3, the plane $P_1$ is the plane of the page, thus the straight portion 52 and the first curved portion 60 are shown in cross-section, while the second curved portion 62 and the third curved portion 64, which are out of the plane $P_1$, are not shown in cross-section.

As further shown in FIG. 3, the catheter 50 forms a lumen 72 extending from a proximal end 74 of the straight portion 52 to the opening 56 at the distal end 58 of hook portion 54. In some embodiments, the lumen 72 can have a diameter D as small as 1 French unit (Fr), 2 Fr, 3 Fr, 4 Fr, 5 Fr, or 6 Fr, or as large as 7 Fr, 8 Fr, 9 Fr, 10 Fr, 11 Fr, or 12 Fr, or any value between any two of the foregoing values such as, for example, 1 Fr to 12 Fr, 2 Fr to 11 Fr, 3 Fr to 10 Fr, 4 Fr to 9 Fr, 5 Fr to 8 Fr, 6 Fr to 7 Fr, 6 Fr to 9 Fr or 7 Fr to 9 Fr. A portion of the lumen 72 extending through the straight portion 52 defines an axis A. It has been found that a diameter D of the lumen 72 equal to or greater than 6 Fr, such as 6 Fr to 9 Fr, may be required to accommodate the lead 14 when the fixation element 24 is an active fixation element as described above because such leads tend to have larger diameters.

As shown in FIG. 3, as the hook portion 54 curves around, it defines a bottom 76 of the hook portion 54. The bottom 76 is a point of the hook portion 54 touching a plane $P_2$ that is farthest from the distal end 66 of the straight portion 52, the plane $P_2$ being perpendicular to both the plane $P_1$ and the axis A. In some embodiments, as shown in FIG. 3, the first curved portion 60 can include the bottom 76 of the hook portion 54.

In some embodiments, the first curved portion 60 and the second curved portion 62 define a compound curve when projected onto the plane $P_1$, as shown in FIG. 3. As shown in FIG. 3, the third curved portion 64 has a reversal of curvature from the compound curve of the first curved portion 60 and the second curved portion 62 when projected on the plane $P_1$.

In some embodiments, a radius of curvature along the first curved portion 60 and the second curved portion 62 is greater than 17 millimeters. It has been found that a radius of curvature less than 17 millimeters along the first curved portion 60 or the second curved portion 62 can impede the transfer of torque to the fixation element 24 (FIG. 1) during implantation, particularly when the fixation element 24 is an active fixation element, as described above. In some embodiments, a radius of curvature along the third curved portion 64 is greater than 10 millimeters. In some other embodiments, the radius of curvature along the entire hook portion 54 is greater than 17 millimeters. In some embodiments, a length of the first curved portion 60 is greater than a length of the second curved portion 62.

FIG. 4 is a bottom view of the catheter 50 shown in FIG. 3, according to some embodiments of this disclosure. As shown in FIG. 4, the first curved portion 60 lies within the plane $P_1$. The second curved portion 62 curves away from the plane $P_1$ as it extends from the distal end 68 of the first curved portion 60. The third curved portion 64 curves back toward the plane $P_1$ as it extends from the distal end 70 of the second curved portion 62.

FIG. 5 is another side view of the catheter 50 shown in FIGS. 3 and 4, according to some embodiments of this disclosure. In FIG. 5, the catheter 50 is shown rotated 90 degrees about the axis A from FIG. 3. As shown in FIG. 5, the straight portion 52 and the first curved portion 60 lie within the plane $P_1$, the second curved portion 62 curves away from the plane $P_1$, and the third curved portion 64 curves back toward the plane $P_1$.

A system for delivering a medical electrical lead to the bundle of His 34 within the right atrium 26 can include the catheter 50 according to any of the embodiments described above, and the lead 14 configured to pass through the lumen 72 of the catheter 50. In some embodiments, the lead 14 can include the fixation element 24. In some embodiments, the fixation element 24 is an active fixation element, as described above.

Considering FIGS. 1-5 together, a method of implanting the lead 14 to stimulate the bundle of His 34 can include introducing the catheter 50 transvascularly through the superior vena cava 36 and into the right atrium 26 of the heart 16, the hook portion 54 of the catheter 50 configured such that the opening 56 at the distal end 58 of the hook portion 54 is disposed perpendicularly to a portion of the atrioventricular septum 28 adjacent to the bundle of His 34. The fixation element 24 on the distal end 22 of the lead 14 can be extended from the opening 56. The tissue of the target site along the atrioventricular septum 28 can be located and the fixation element 24 deployed in the tissue of the target site to implant the lead 14 in contact with the bundle of His 34. The catheter 50 can be removed from over the lead 14.

In some embodiments, introducing the catheter 50 transvascularly into the heart 16 can include disposing the hook portion 54 within the heart 16 such that it extends down a lateral wall of the superior vena cava 36, and across the right atrium 26 so that the opening 56 at the distal end 58 of the hook portion 54 is disposed perpendicularly to a portion of the atrioventricular septum 28 adjacent to the bundle of His 34.

Figure 6:
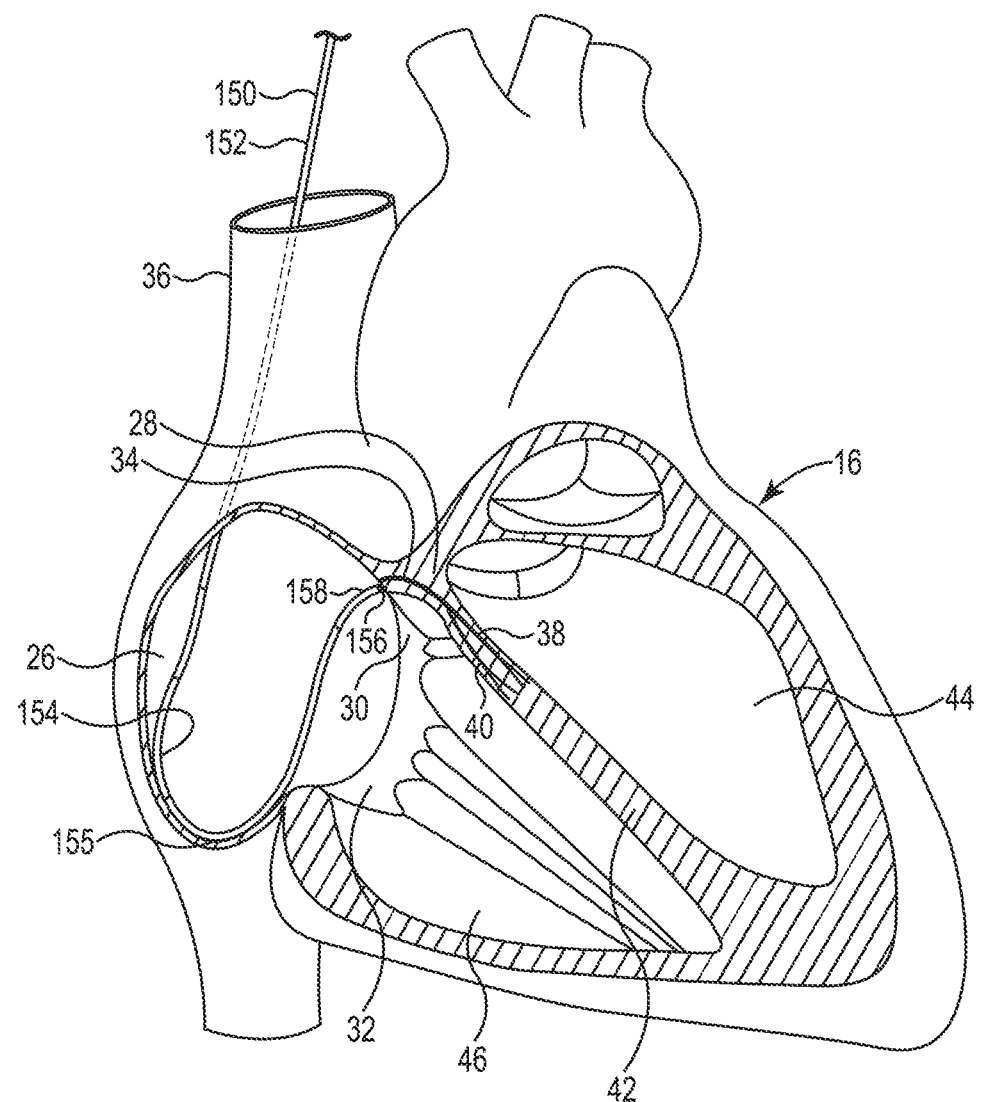
FIG. 6 is a schematic diagram of another catheter for delivering a medical electrical lead to a bundle of His from within the right atrium, according to some embodiments of this disclosure.

FIG. 6 is a schematic diagram of another catheter for delivering a medical electrical lead to a bundle of His from within the right atrium, according to some embodiments of this disclosure. FIG. 6 shows a catheter 150 including a straight portion 152 and a hook portion 154. The hook portion 154 can project from the straight portion 152. The catheter 150 can be introduced transvascularly into the heart 16 as described above for the lead 14 in reference to FIG. 1. The catheter 150 is configured, as described below in reference to FIGS. 7-9, to extend down a right lateral wall of the right atrium 26 toward a floor 155 of the right atrium 26, and extend anterio-medial away from the floor 155 to so that an opening 156 at a distal end 158 of the hook portion 154 is disposed perpendicularly to a portion of the atrioventricular septum 28 adjacent to the bundle of His 34. So oriented, the lead 14 passing through the catheter 150 can be accurately delivered to the target site for implantation. In some embodiments, the catheter 150 may be configured to contact the floor 155. In some other embodiments, the catheter 150 may be configured to approach, but not contact, the floor 155.

Figure 7:
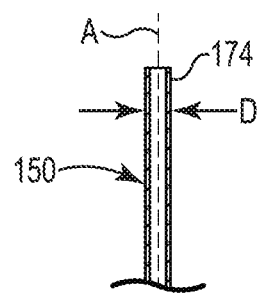
FIG. 7 is a side view of the catheter of FIG. 6 for delivering a medical electrical lead to a bundle of His from within a right atrium, according to some embodiments of this disclosure.
Figure 7:
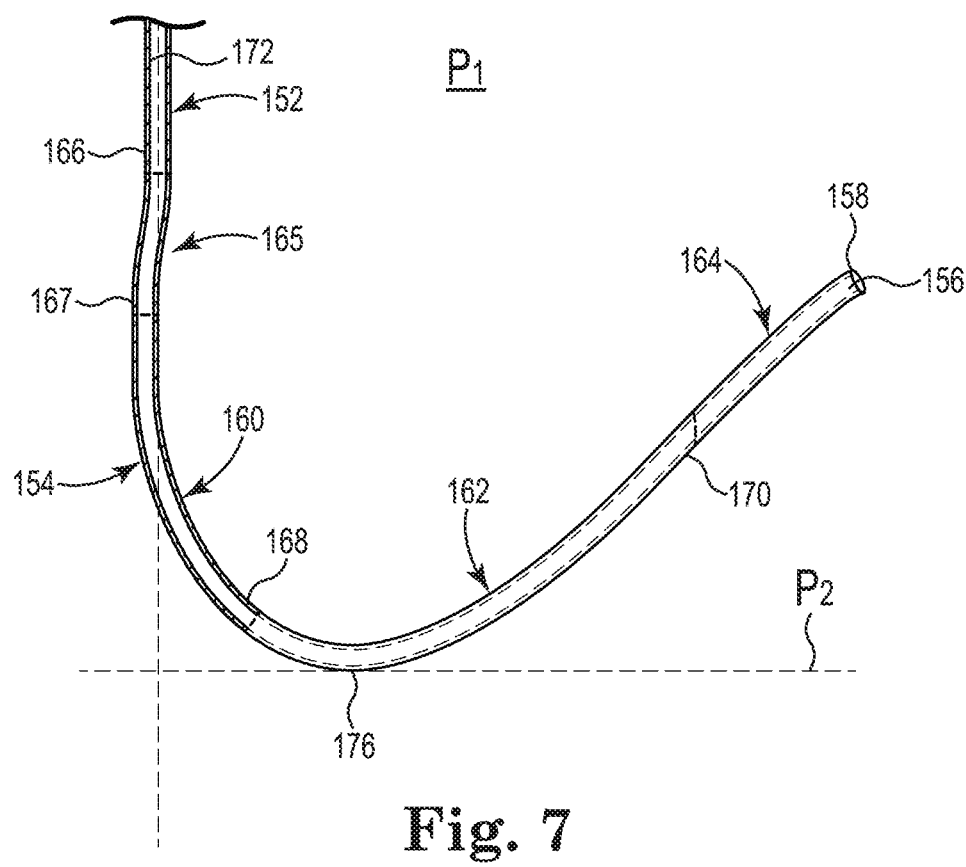

FIG. 7 is a side view of the catheter 150 of FIG. 6 for delivering a medical electrical lead to a bundle of His from within a right atrium, according to some embodiments of this disclosure. FIG. 7 shows the catheter 150 including the straight portion 152 and the hook portion 154. The hook portion 154 can include a first curved portion 160, a second curved portion 162, a third curved portion 164, and a fourth curved portion 165. The hook portion 154 can project from a distal end 166 of the straight portion 152. The first curved portion 160 can extend from a distal end 167 of the fourth curved portion 165. The second curved portion 162 can extend from a distal end 168 of the first curved portion 160. The third curved portion 164 can extend from a distal end 170 of the second curved portion 162. In some embodiments, the third curved portion 164 can include the opening 156 at the distal end 158 of the hook portion 154, as shown in FIG. 7. The fourth curved portion 165 can extend from the distal end 166 of the straight portion 152. The straight portion 152, the fourth curved portion 165, and the first curved portion 160 can define a plane $P_1$. Thus, the fourth curved portion 165 is coplanar with the straight portion 152 and the first curved portion 160. As shown in FIG. 7, the fourth curved portion 165 has a reversal of curvature from the first curved portion 160.

Figure 8:
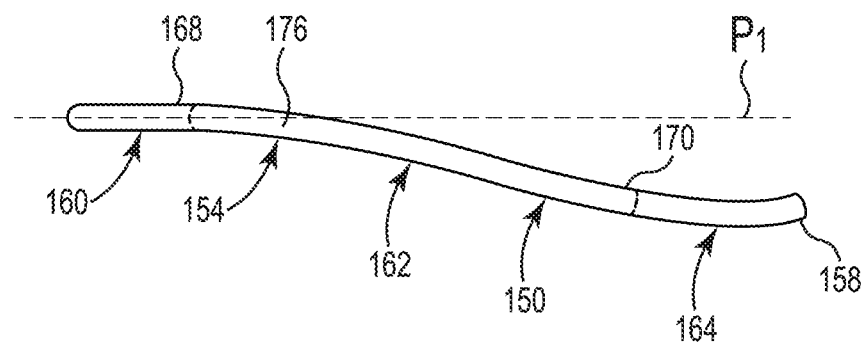
FIG. 8 is a bottom view of the catheter shown in FIG. 7, according to some embodiments of this disclosure.
Figure 9:
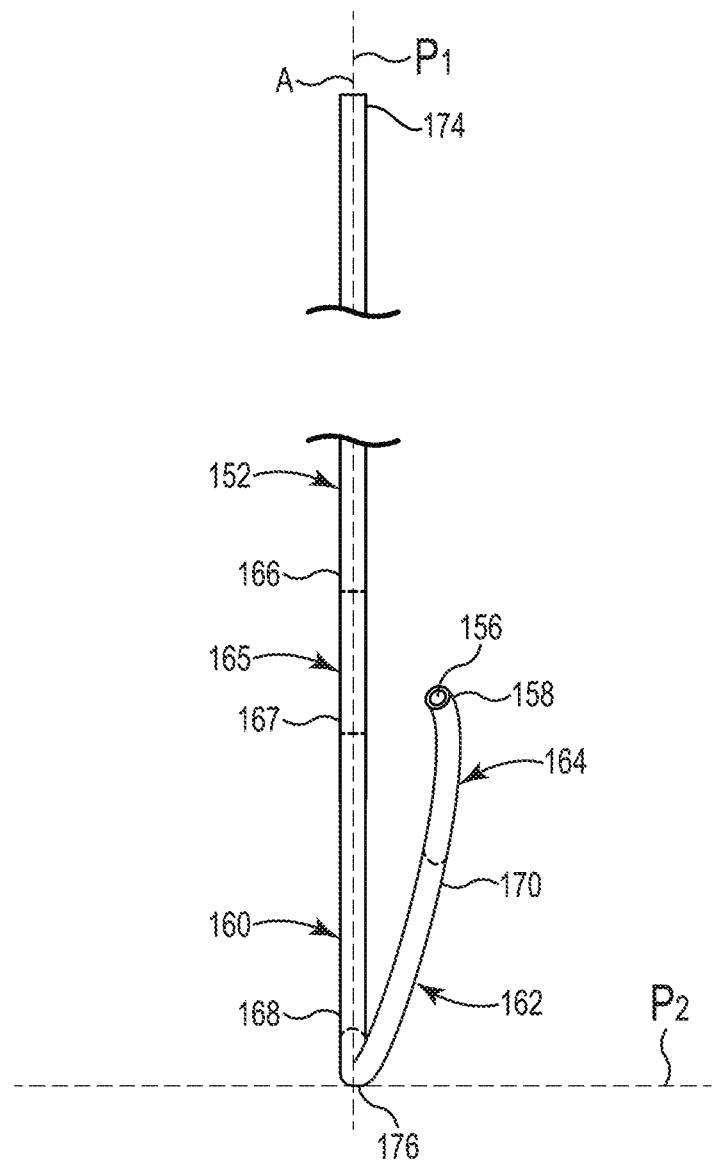
FIG. 9 is another side view of the catheter shown in FIGS. 7 and 8, according to some embodiments of this disclosure.

The second curved portion 162 can curve away from the plane $P_1$, as shown in FIGS. 8 and 9, described below. The third curved portion 164 can curve back toward the plane $P_1$, as also shown in FIGS. 8 and 9. In FIG. 7, the plane $P_1$ is the plane of the page, thus the straight portion 152, the fourth curved portion 165, and the first curved portion 160 are shown in cross-section, while the second curved portion 162 and the third curved portion 169, which are out of the plane $P_1$, are not shown in cross-section.

As further shown in FIG. 7, the catheter 150 forms a lumen 172 extending from a proximal end 174 of the straight portion 152 to the opening 156 at a distal end 158 of the third curved portion 164. In some embodiments, the lumen 172 can have a diameter D as small as 1 French unit (Fr), 2 Fr, 3 Fr, 4 Fr, 5 Fr, or 6 Fr, or as large as 7 Fr, 8 Fr, 9 Fr, 10 Fr, 11 Fr, or 12 Fr, or any value between any two of the foregoing values such as, for example, 1 Fr to 12 Fr, 2 Fr to 11 Fr, 3 Fr to 10 Fr, 4 Fr to 9 Fr, 5 Fr to 8 Fr, 6 Fr to 7 Fr, 6 Fr to 9 Fr or 7 Fr to 9 Fr. A portion of the lumen 172 extending through the straight portion 152 defines an axis A. It has been found that a diameter D of the lumen 172 equal to or greater than 6 Fr, such as 6 Fr to 9 Fr, may be required to accommodate the lead 14 when the fixation element 24 is an active fixation element because such leads tend to have larger diameters.

As shown in FIG. 7, as the hook portion 154 curves around, it defines a bottom 176 of the hook portion 154. The bottom 176 is a point of the hook portion 154 touching a plane $P_2$ that is farthest from the distal end 166 of the straight portion 152, the plane $P_2$ being perpendicular to both the plane $P_1$ and the axis A. In some embodiments, as shown in FIG. 7, the second curved portion 162 can include the bottom 176 of the hook portion 154.

In some embodiments, the first curved portion 160 and the second curved portion 162 define a compound curve when projected onto the plane $P_1$, as shown in FIG. 7. In some embodiments, a radius of curvature along the first curved portion 160, and the second curved portion 162 is greater than 17 millimeters. It has been found that a radius of curvature less than 17 millimeters along the first curved portion 160 and the second curved portion 162 can impede the transfer of torque to the fixation element 24 (FIG. 1) during implantation, particularly when the fixation element 24 is an active fixation element, as described above. In some embodiments, a radius of curvature along the third curved portion 164 is greater than 10 millimeters. In some other embodiments, the radius of curvature along the entire hook portion 154 is greater than 17 millimeters. In some embodiments, a length of the second curved portion 162 is greater than a length of the first curved portion 160.

FIG. 8 is a bottom view of the catheter 150 shown in FIG. 7, according to some embodiments of this disclosure. As shown in FIG. 8, the first curved portion 160 lies within the plane $P_1$. The second curved portion 162 curves away from the plane $P_1$ as it extends from the distal end 168 of the first curved portion 160. The third curved portion 164 curves back toward the plane $P_1$ as it extends from the distal end 170 of the second curved portion 162.

FIG. 9 is another side view of the catheter 150 shown in FIGS. 7 and 8, according to some embodiments of this disclosure. In FIG. 9, the catheter 150 is shown rotated 90 degrees about the axis A from FIG. 7. As shown in FIG. 9, the straight portion 152, the fourth curved portion 165, and the first curved portion 160 lie within the plane $P_1$, the second curved portion 162 curves away from the plane $P_1$, and the third curved portion 164 curves back toward the plane $P_1$.

A system for delivering a medical electrical lead to the bundle of His 34 within the right atrium 26 can include the catheter 150 according to any of the embodiments described above, and the lead 14 configured to pass through the lumen 172 of the catheter 150. In some embodiments, the lead 14 can include the fixation element 24. In some embodiments, the fixation element 24 is an active fixation element, as described above.

Considering FIGS. 1 and 6-9 together, a method of implanting the lead 14 to stimulate the bundle of His 34 can include introducing the catheter 150 transvascularly through the superior vena cava 36 and into the right atrium 26 of the heart 16, the hook portion 154 of the catheter 150 configured such that the opening 156 at the distal end 158 of the hook portion 154 is disposed perpendicularly to a portion of the atrioventricular septum 28 adjacent to the bundle of His 34. The fixation element 24 on the distal end 22 of the lead 14 can be extended from the opening 56. The tissue of the target site along the atrioventricular septum 28 can be located and the fixation element 24 deployed in the tissue of the target site to implant the lead 14 in contact with the bundle of His 34. The catheter 50 can be removed from over the lead 14.

In some embodiments, introducing the catheter 150 transvascularly into the heart 16 can include disposing the hook portion 154 within the heart 16 such that it extends down a right lateral wall of the right atrium 26 toward the floor 155 of the right atrium 26, and extends anterio-medial away from the floor 155 of the right atrium 26 so that the opening 156 at the distal end 158 of the hook portion 154 is disposed perpendicularly to the portion of the atrioventricular septum 28 adjacent to the bundle of His 34.

Figure 10:
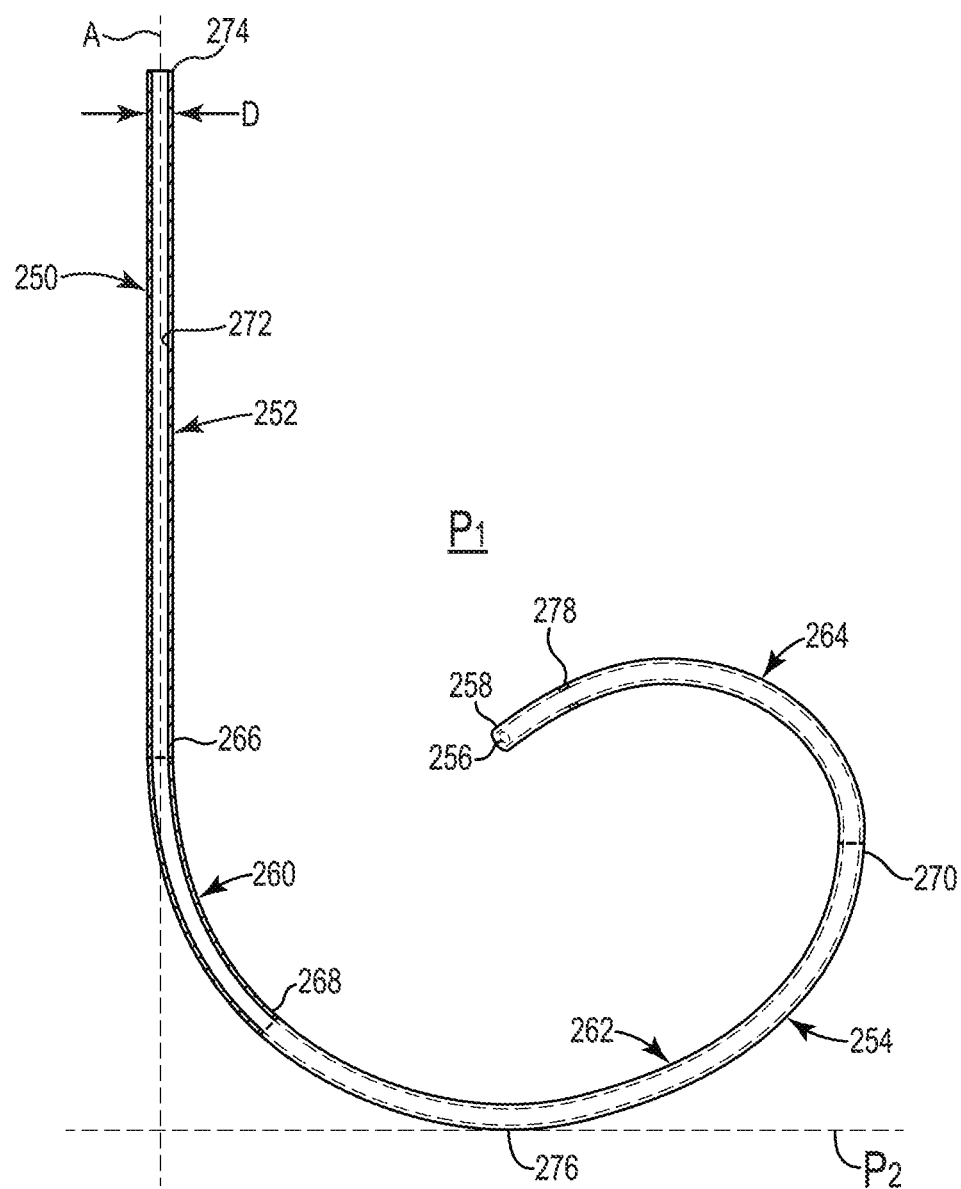
FIG. 10 is a side view of another catheter for delivering a medical electrical lead to a bundle of His from within a right atrium, according to some embodiments of this disclosure.

FIG. 10 is a side view another catheter for delivering a medical electrical lead to the bundle of His from within the right atrium, according to some embodiments of this disclosure. FIG. 10 shows a catheter 250 including a straight portion 252 and a hook portion 254. The hook portion 254 can include a first curved portion 260, a second curved portion 262, a third curved portion 264. The hook portion 254 can project from a distal end 266 of the straight portion 252. The first curved portion 260 can extend from the distal end 266 of the straight portion 252. The second curved portion 262 can extend from a distal end 268 of the first curved portion 260. The third curved portion 264 can extend from a distal end 270 of the second curved portion 262. The third curved portion 264 can include an opening 256 (FIG. 11) at a distal end 258 of the hook portion 254, as shown in FIG. 10. The straight portion 252 and the first curved portion 260 can define a plane $P_1$. As the hook portion 254 curves around, it defines a bottom 276 of the hook portion 254. The bottom 276 is a point of the hook portion 254 touching a plane $P_2$ that is farthest from the distal end 266 of the straight portion 252, the plane $P_2$ being perpendicular to both the plane $P_1$ and the axis A. In some embodiments, as shown in FIG. 10, the second curved portion 262 can include the bottom 276 of the hook portion 254.

Figure 11:
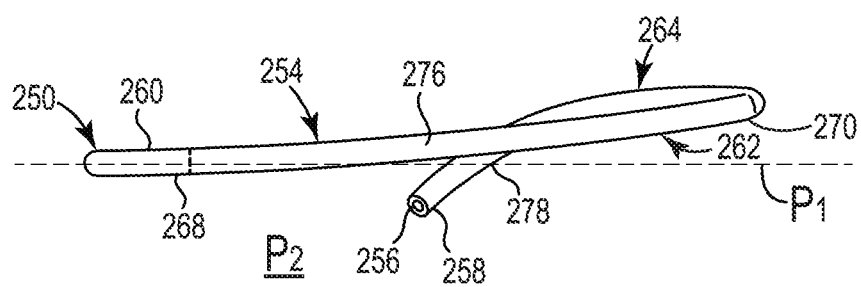
FIG. 11 is a bottom view of the catheter shown in FIG. 10, according to some embodiments of this disclosure.
Figure 12:
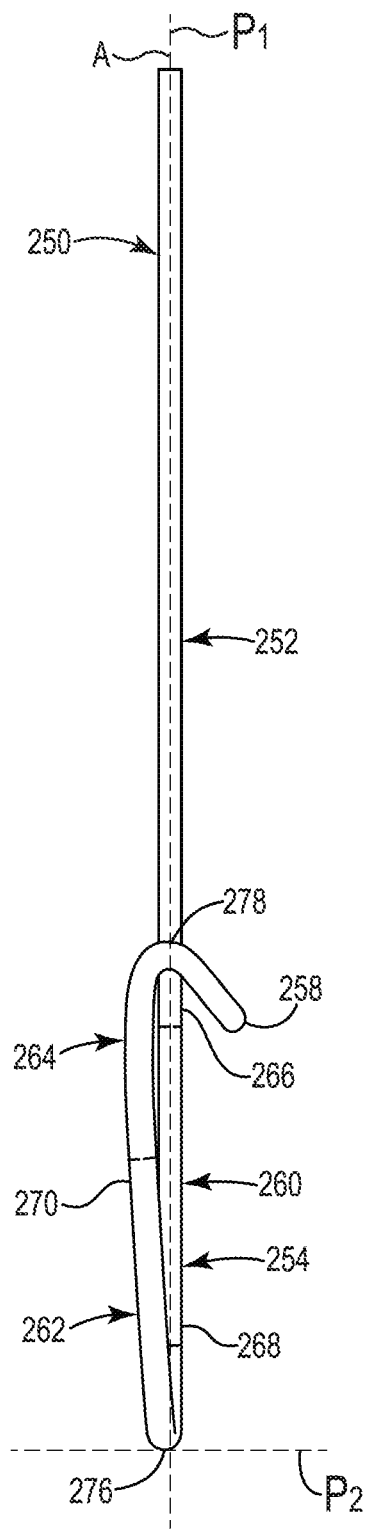
FIG. 12 is another side view of the catheter shown in FIGS. 10 and 11, according to some embodiments of this disclosure.

The second curved portion 262 can curve away from the plane $P_1$ and as shown in FIGS. 11 and 12 and described below. The third curved portion 264 curves back toward the plane $P_1$ and extends project the plane $P_1$, as also shown in FIGS. 11 and 12. In FIG. 10, the plane $P_1$ is the plane of the page, thus the straight portion 252 and the first curved portion 260 are shown in cross-section, while the second curved portion 262 and the third curved portion 264 are not shown in cross-section because they are out of the plane $P_1$ except where the third curved portion 264 crosses the plane $P_1$ at cross-over point 278. The first curved portion 260 and the second curved portion 262 define a compound curve when projected onto the plane $P_1$, as shown in FIG. 10. Unlike the embodiments described above, the third curved portion 264 does not have a reversal of curvature from the compound curve of the first curved portion 260 and the second curved portion 262, but continues the compound curve when projected on the plane $P_1$, curving generally back toward the first curved portion 260.

As further shown in FIG. 10, the catheter 250 forms a lumen 272 extending from a proximal end 274 of the straight portion 252 to the opening 256 at the distal end 258 of hook portion 254. In some embodiments, the lumen 272 can have a diameter D as small as 1 French unit (Fr), 2 Fr, 3 Fr, 4 Fr, 5 Fr, or 6 Fr, or as large as 7 Fr, 8 Fr, 9 Fr, 10 Fr, 11 Fr, or 12 Fr, or any value between any two of the foregoing values such as, for example, 1 Fr to 12 Fr, 2 Fr to 11 Fr, 3 Fr to 10 Fr, 4 Fr to 9 Fr, 5 Fr to 8 Fr, 6 Fr to 7 Fr, 6 Fr to 9 Fr or 7 Fr to 9 Fr. A portion of the lumen 272 extending through the straight portion 252 defines an axis A. It has been found that a diameter D of the lumen 272 equal to or greater than 6 Fr, such as 6 Fr to 9 Fr, may be required to accommodate the lead 14 when the fixation element 24 is an active fixation element as described above because such leads tend to have larger diameters.

In some embodiments, a radius of curvature when projected onto the plane $P_1$ along the first curved portion 260 and the second curved portion 262 is greater than 17 millimeters. It has been found that a radius of curvature less than 17 millimeters along the first curved portion 260 or the second curved portion 262 can impede the transfer of torque to the fixation element 24 (FIG. 1) during implantation, particularly when the fixation element 24 is an active fixation element, as described above. In some embodiments, a radius of curvature along the third curved portion 264 is greater than 10 millimeters. In some other embodiments, the radius of curvature along the entire hook portion 254 is greater than 17 millimeters.

FIG. 11 is a bottom view of the catheter 250 shown in FIG. 10, according to some embodiments of this disclosure. As shown in FIG. 11, the first curved portion 260 lies within the plane $P_1$. The second curved portion 262 curves away from the plane $P_1$ as it extends from the distal end 268 of the first curved portion 260. The third curved portion 264 curves back toward the plane $P_1$ and crosses the plane $P_1$ at cross-over point 278 as it extends from the distal end 270 of the second curved portion 262 and generally toward the first curved portion 260.

FIG. 12 is another side view of the catheter 250 shown in FIGS. 10 and 11, according to some embodiments of this disclosure. In FIG. 12, the catheter 250 is shown rotated 90 degrees about the axis A from FIG. 10. As shown in FIG. 12, the straight portion 252 and the first curved portion 260 lie within the plane $P_1$, the second curved portion 262 curves away from the plane $P_1$, and the third curved portion 264 curves back across the plane $P_1$, crossing the plane $P_1$ at cross-over point 278.

A system for delivering a medical electrical lead to the bundle of His 34 within the right atrium 26 can include the catheter 250 according to any of the embodiments described above, and the lead 14 configured to pass through the lumen 272 of the catheter 250. In some embodiments, the lead 14 can include the fixation element 24. In some embodiments, the fixation element 24 is an active fixation element, as described above.

Considering FIGS. 1 and 10-12 together, a method of implanting the lead 14 to stimulate the bundle of His 34 can include introducing the catheter 250 transvascularly through the superior vena cava 36 and into the right atrium 26 of the heart 16, the hook portion 254 of the catheter 250 configured such that the opening 256 at the distal end 258 of the hook portion 254 is disposed perpendicularly to a portion of the atrioventricular septum 28 adjacent to the bundle of His 34 when the distal end 258 is in contact with the tissue of the target site. The fixation element 24 on the distal end 22 of the lead 14 can be extended from the opening 256. The tissue of the target site along the atrioventricular septum 28 can be located. As the fixation element 24 is deployed in the tissue of the target site to implant the lead 14 in contact with the bundle of His 34, the curvature of the hook portion 254 combined with the elasticity of the catheter 250 can force the distal end 258 against the tissue and provide for more stable deployment of the fixation element 24. The catheter 250 can be removed from over the lead 14.

Various modifications and additions can be made to the embodiments discussed without departing from the scope of this disclosure. For example, while the embodiments described above refer to particular features, the scope of this disclosure also includes embodiments having different combinations of features and embodiments that do not include all of the described features. Accordingly, the scope of this disclosure is intended to embrace all such alternatives, modifications, and variations as fall within the scope of the claims, together with all equivalents thereof.

We claim:

1. A catheter for delivering a medical electrical lead to a bundle of His from within a right atrium of a heart, the catheter comprising:
   a straight portion; and
   a hook portion projecting from a distal end of the straight portion, the hook portion including:
      a first curved portion, the straight portion and the first curved portion defining a plane, the first curved portion having a radius of curvature greater than 17 millimeters;
      a second curved portion extending from a distal end of the first curved portion, the second curved portion curving away from the plane, the second curved portion having a radius of curvature greater than 17 millimeters; and
      a third curved portion extending from a distal end of the second curved portion, the third curved portion curving toward the plane, wherein the first curved portion, the second curved portion and the third curved portion define a compound curve with no reversal of curvature when projected onto the plane, the third curved portion extending toward the first curved portion and across the plane,
   the catheter forming a lumen extending from a proximal end of the straight portion to an opening at a distal end of the third curved portion, wherein the lumen has a diameter of 6 Fr to 9 Fr.

2. The catheter of claim 1, wherein the first curved portion and the second curved portion define a compound curve when projected onto the plane, and the third curved portion has a reversal of curvature from the compound curve when projected onto the plane.

3. The catheter of claim 1, wherein the catheter is configured to be introduced transvascularly into the heart, extend down a lateral wall of a superior vena cava, and across the right atrium so that the opening at a distal end of the hook portion is disposed perpendicularly to a portion of an atrioventricular septum adjacent to the bundle of His.

4. The catheter of claim 3, wherein the first curved portion includes a bottom of the hook portion.

5. The catheter of claim 3, wherein the first curved portion extends from the distal end of the straight portion.

6. The catheter of claim 1, wherein a length of the first curved portion is greater than a length of the second curved portion.

7. The catheter of claim 1, wherein the catheter is configured to be introduced transvascularly into the heart, extend down a right lateral wall of the right atrium toward a floor of the right atrium, and extend anterio-medial away from the floor of the right atrium so that the opening at the distal end of the hook portion is disposed perpendicularly to a portion of an atrioventricular septum adjacent to the bundle of His.

8. The catheter of claim 7, wherein the second curved portion includes a bottom of the hook portion.

9. The catheter of claim 7, further including a fourth curved portion extending from the distal end of the straight portion, the first curved portion extending from a distal end of the fourth curved portion, the fourth curved portion coplanar with the first curved portion and having a reversal of curvature from the first curved portion when projected onto the plane.

10. The catheter of claim 7, wherein a length of the second curved portion is greater than a length of the first curved portion.

11. The catheter of claim 1, wherein the hook portion has a radius of curvature greater than 17 millimeters.

12. A system for delivering a medical electrical lead to a bundle of His from within a right atrium of a heart, the system comprising:
   a catheter including:
      a straight portion; and
      a hook portion projecting from a distal end of the straight portion, the hook portion including:

a first curved portion, the straight portion and the first curved portion defining a plane, the first curved portion having a radius of curvature greater than 17 millimeters;

a second curved portion extending from a distal end of the first curved portion, the second curved portion curving away from the plane, the second curved portion having a radius of curvature greater than 17 millimeters; and a third curved portion extending from a distal end of the second curved portion, the third curved portion curving toward the plane, wherein the first curved portion, the second curved portion and the third curved portion define a compound curve with no reversal of curvature when projected onto the plane, the third curved portion extending toward the first curved portion and across the plane, the catheter forming a lumen extending from a proximal end of the straight portion to an opening at a distal end of the third curved portion, wherein the lumen has a diameter of 6 Fr to 9 Fr; and the medical electrical lead configured to pass through the lumen.

13. The system of claim 12, wherein the medical electrical lead includes an active fixation element.

14. The system of claim 12, wherein the first curved portion and the second curved portion define a compound curve when projected onto the plane, and the third curved portion has a reversal of curvature from the compound curve when projected onto the plane.

15. The system of claim 12, further including a fourth curved portion extending from the distal end of the straight portion, the first curved portion extending from a distal end of the fourth curved portion, the fourth curved portion coplanar with the first curved portion and having a reversal of curvature from the first curved portion when projected onto the plane.

* * * * *